(12) United States Patent
Esser et al.

(10) Patent No.: US 6,277,840 B1
(45) Date of Patent: Aug. 21, 2001

(54) NEUROKININ ANTAGONISTS, PROCESSES FOR PREPARING THEM AND PHARMACEUTICAL COMPOSITIONS CONTAINING THESE COMPOUNDS

(75) Inventors: Franz Esser, Ingelheim; Gerd Schnorrenberg, Biberach/Riss; Horst Dollinger, Ingelheim; Sven Luettke, Ockenheim; Birgit Jung, Schwabenheim; Georg Speck, Ingelheim, all of (DE)

(73) Assignee: Boehringer Ingelheim Pharma KG, Ingelheim (DE)

( * ) Notice: Subject to any disclaimer, the term of this patent is extended or adjusted under 35 U.S.C. 154(b) by 0 days.

(21) Appl. No.: 09/566,754

(22) Filed: May 9, 2000

Related U.S. Application Data

(62) Division of application No. 09/320,974, filed on May 27, 1999, now Pat. No. 6,103,719.

(30) Foreign Application Priority Data

May 30, 1998 (DE) .............................. 198 24 470

(51) Int. Cl.$^7$ .................. C07D 295/125; C07D 401/06; C07D 403/06; A61K 31/496; C07P 267/22
(52) U.S. Cl. .................. 514/183; 514/218; 514/256; 514/341; 540/467; 540/470; 540/553; 544/330; 546/223
(58) Field of Search .................. 544/330; 546/223; 514/183, 218, 256, 341; 540/467, 470, 553

(56) References Cited

U.S. PATENT DOCUMENTS

| | | | |
|---|---|---|---|
| 4,563,466 | * 1/1986 | Archibald et al. | 514/319 |
| 5,607,936 | 3/1997 | Chiang | 514/255 |
| 5,654,316 | 8/1997 | Carruthers | 514/307 |
| 5,710,155 | 1/1998 | Schnorrenberg | 514/255 |
| 5,981,520 | 11/1999 | Shue | 514/212 |

OTHER PUBLICATIONS

Lowe, J.A. et al, "Annual Reports in Medicinal Chemistry, vol. 28", 1993, 99–105.*

* cited by examiner

Primary Examiner—Mukund J. Shah
Assistant Examiner—Thomas C McKenzie
(74) Attorney, Agent, or Firm—Robert P. Raymond; Anthony P. Bottino; Alan R. Stempel

(57) ABSTRACT

The invention relates to new compounds of general formula I

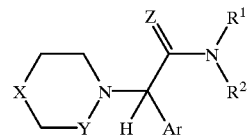

or the pharmaceutically acceptable salts thereof, wherein X=N—$R^3$ or CH—$R^4$,
Y=$CH_2$ or $(CH_2)_2$,
Z=O or $H_2$;

and $R^1$, $R^2$, $R^3$, $R^4$ and Ar have the meanings given in the specification, and the preparation and use thereof. The new compounds are valuable neurokinin (tachykinin) antagonists.

7 Claims, No Drawings

NEUROKININ ANTAGONISTS, PROCESSES FOR PREPARING THEM AND PHARMACEUTICAL COMPOSITIONS CONTAINING THESE COMPOUNDS

This application is a division of application ser. No. 09/320,974, filed May 27, 1999, now U.S. Pat. No. 6,103,719.

The invention relates to new guanidine and amidine derivatives of general formula I

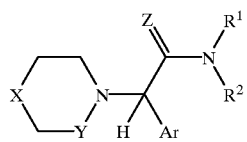

and the pharmaceutically acceptable salts thereof, processes for preparing them and pharmaceutical compositions containing these compounds. The compounds are valuable neurokinin (tachykinin) antagonists.

The abbreviations used in this specification and claims are explained as follows:

Boc=t-butyloxycarbonyl
DC=thin layer chromatogram
DMF=dimethylformamide
EE=ethyl acetate
FAB-MS fast atom bombardment mass spectroscopy
RT=room temperature
TBTU=O-benzotriazolyl-tetramethyluronium tetrafluoroborate
TEA=triethylamine
THF=tetrahydrofuran A simplified format is used for the formulae. In the representations of compounds, all $CH_3$ substituents are indicated by a hyphen, e.g.

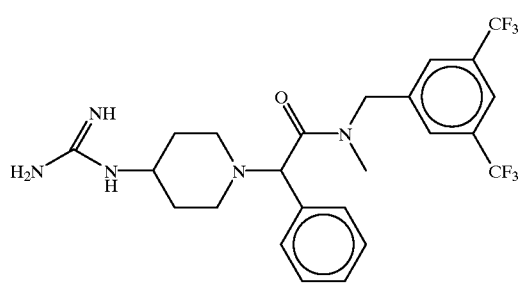

denotes

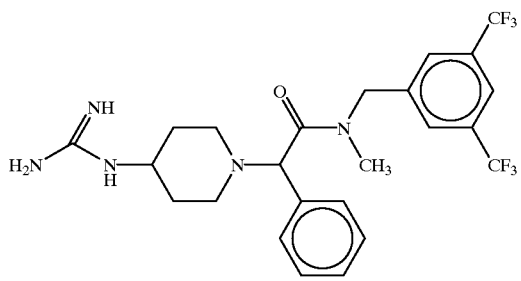

The invention relates to new guanidine and amidine derivatives of general formula I

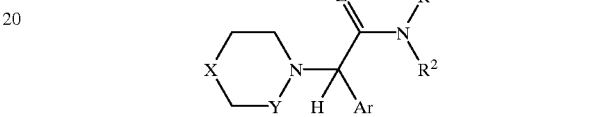

or the pharmaceutically acceptable salts thereof, wherein
X denotes $N-R^3$ or $CH-R^4$, wherein $R^3$ denotes

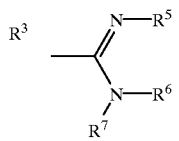

wherein $R^5$, $R^6$ and $R^7$ independently of one another denote H, alkyl, cycloalkyl, alkenyl, aryl, aralkyl, alkanoyl, benzoyl, heteroaryl, dialkylamino, dialkylaminoalkyl, trialkylammoniumalkyl, cyano, alkyloxycarbonyl, aralkyloxycarbonyl, OH, O-alkyl or O-aryl, wherein the alkyl groups contain 1 to 5 carbon atoms, the cycloalkyl groups contain 3 to 6 carbon atoms, the alkenyl groups, contain 2 to 5 carbon atoms, aryl denotes phenyl, or phenyl or naphthyl substituted by methyl or halogen (F, Cl, Br, I);

or $R^5$ and $R^6$ or $R^6$ and $R^7$ together form the group $(CH_2)_2-$, $-(CH_2)_3-$, $-(CH_2)_4-$, $(CH_2)_5-$ or $-(CH_2)_2O(CH_2)_2$;

$R^3$ denotes

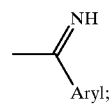

and $R^4$ denotes

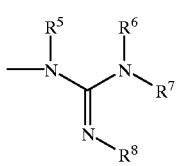

wherein $R^5$ to $R^7$ are as hereinbefore defined and $R^8$=H, alkyl with 1 to 5 carbon atoms or cycloalkyl with 3 to 6 carbon atoms or $R^7+R^8$ together form the group —(CH$_2$)$_2$—, —(CH$_2$)$_3$—, —(CH$_2$)$_4$—, —(CH$_2$)$_5$— or —(CH$_2$)$_2$ O(CH$_2$)$_2$—;

or $R^4$ denotes

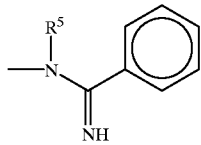

wherein $R^5$ is as hereinbefore defined;

Y denotes CH$_2$ or (CH$_2$)$_2$;

Z denotes C or H$_2$;

Ar denotes unsubstituted or mono- to 5-substituted phenyl, or unsubstituted or mono- or disubstituted naphthyl [wherein the substituents of the phenyl and naphthyl independently of one another denote halogen (F, Cl, Br, I), OH, (C$_{1-4}$)alkyl, O—(C$_{1-4}$)alkyl, CF$_3$, OCF$_3$ or NR$^9$R$^{10}$ (wherein R$^9$ and R$^{10}$ independently of one another denote H, methyl or acetyl)] or Ar is phenyl substituted by —OCH$_2$O— or —O(CH$_2$)$_2$O—;

$R^1$ denotes phenyl(C$_{1-4}$)alkyl or phenyl(C$_{1-4}$)alkanoyl or naphthyl(C$_{1-4}$)alkyl or naphthylacetyl, wherein phenyl may be substituted by 1 to 3 substituents, wherein the substituents independently of one another denote halogen (F, Cl, Br, I), (C$_{1-4}$)alkyl, O—(C$_{1-4}$)alkyl, CF$_3$, OCF$_3$ or NR$^{19}$R$^{20}$ (wherein R$^{19}$ and R$^{20}$ independently of one another denote H, methyl or acetyl); and $R^2$ denotes H, (C$_{1-4}$)alkyl, (C$_{3-6}$)cycloalkyl, CH$_2$COOH, —CH$_2$C(O)NH$_2$, OH or phenyl(C$_{1-4}$)alkyl.

The compounds according to the invention are valuable neurokinin (tachykinin) antagonists which have both substance P antagonism and also neurokinin-A- or neurokinin-B-antagonistic properties. They are useful for the treatment and prevention of neurokinin-mediated diseases.

Compounds of general formula I may contain acid groups, mainly carboxyl groups, and/or basic groups such as amino functions, for example. Compounds of general formula I may therefore occur as internal salts, salts with pharmaceutically acceptable inorganic acids such as hydrochloric acid, sulphuric acid, phosphoric acid, sulphonic acid or organic acids (such as, for example, maleic acid, fumaric acid, citric acid, tartaric acid or acetic acid) or as salts with pharmaceutically acceptable bases such as alkali metal or alkaline earth metal hydroxides or carbonates, zinc or ammonium hydroxides or organic amines such as e.g. diethylamine, triethylamine, triethanolamine, etc.

The compounds according to the invention may occur as racemates, but may also be obtained as pure enantiomers, i.e. in the (R) or (S) form. Compounds which occur as racemates or in the (S) form are preferred.

Results of investigations into the compound according to the invention: The receptor affinity for the NK$_1$ receptor (substance P receptor) is determined on human lymphoblastoma cells (IM-9) with cloned NK$_1$ receptors, by measuring the displacement of $^{125}$I-labelled substance P. The K$i$ values thus obtained show the efficacy of the compounds.

| Example no. | K$_i$ [nMol/L] |
|---|---|
| 1 | 0.45 |
| 2 | 0.30 |
| 3 | 0.20 |
| 4 | 0.53 |
| 5 | 6.28 |
| 6 | 0.88 |
| 7 | 1.45 |
| 8 | 0.19 |
| 9 | 0.14 |
| 10 | 0.12 |
| 12 | 0.32 |
| 27 | 1.11 |
| 28 | 4.16 |
| 29 | 0.87 |
| 30 | 0.17 |
| 31 | 8.96 |
| 32 | 0.20 |
| 33 | 13.25 |
| 34 | 0.37 |
| 35 | 0.78 |

The compounds according to the invention are valuable neurokinin (tachykinin) antagonists which have both substance P antagonism and also neurokinin-A- or neurokinin-B-antagonistic properties. They are useful for the treatment and prevention of neurokinin-mediated diseases:

For preventing or treating inflammatory or allergic diseases of the respiratory tract such as asthma, chronic bronchitis, hyperreactive respiratory tract, emphysema, rhinitis, cough, of the eyes, such as conjunctivitis and iritis, of the skin, such as dermatitis in contact eczema, urticaria, psoriasis, sunburn, insect bites, itching, sensitive or hypersensitive skin, of the gastrointestinal tract such as gastric and duodenal ulcers, ulcerative colitis, Crohn's disease, irritable bowel, Hirschsprung's disease, of the joints, such as rheumatoid arthritis, reactive arthritis and Reiter syndrome;

for treating diseases of the central nervous system, such as dementia, Alzheimer's disease, schizophrenia, psychoses, depression, headache (e.g. migraine or tension headaches), epilepsy; Parkinson's disease, stroke, for treating Herpes zoster and postherpetic pain, tumours, collagenoses, dysfunction of the urinary tract, haemorrhoids, nausea and vomiting, triggered by radiation or cytostatic therapy, for example, or movement and pain of all kinds.

The invention therefore also relates to the use of the compounds according to the invention as curative agents and pharmaceutical preparations which contain these compounds. They are preferably used in humans. The compounds according to the invention may be administered by intravenous, subcutaneous, intramuscular, intraperitoneal or intranasal route, by inhalation, by transdermal route, if desired with the aid of iontophoresis or enhancers known from the literature, and by oral route. For parenteral administration the compounds of formula I or the physiologically acceptable salts thereof are brought into solution, suspension or emulsion, optionally with the substances conventionally used for this, such as solubilisers; emulsifiers or other adjuvants. Suitable solvents include, for example: water, physiological saline solutions or alcohols, e.g. ethanol, propandiol or glycerol, sugar solutions such as glucose or mannitol solutions or a mixture of different solvents.

Moreover, the compounds may be administered by means of implants, e.g. of polylactide, polyglycolide or polyhydroxybutyric acid or intranasal preparations.

Preferred compounds of general formula 1 are those wherein

X denotes N—$R^3$ or CH—$R^4$, wherein $R^3$ denotes

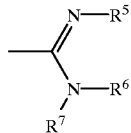

wherein $R^5$, $R^6$ and $R^7$ independently of one another denote H, alkyl, cycloalkyl, aryl, aralkyl, alkanoyl, benzoyl, dialkylamino, dialkylaminoalkyl, trialkylammoniumalkyl, cyano, alkyloxycarbonyl, aralkyloxycarbonyl, OH, O-alkyl or O-aryl, wherein the alkyl groups contain 1 to 4 carbon atoms, the cycloalkyl groups contain 3 to 6 carbon atoms, aryl denotes phenyl or phenyl substituted by methyl or halogen (F, Cl, Br, I);

or $R^5$ and $R^6$ or $R^6$ and $R^7$ together form the group —(CH$_2$)$_2$—, —(CH$_2$)$_3$—, —(CH$_2$)$_4$—, —(CH$_2$)$_5$— or —(CH$_2$)$_2$ O(CH$_2$)$_2$;

or $R^3$ is

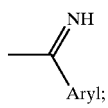

and $R^4$ is

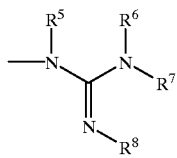

wherein $R^5$ to $R^7$ are as hereinbefore defined and $R^8$=H, alkyl with 1 to 5 carbon atoms or cycloalkyl with 3 to 6 carbon atoms or $R^7$+$R^8$ together form the group —(CH$_2$)$_2$—, —(CH$_2$)$_3$—, —(CH$_2$)$_4$—, —(CH$_2$)$_5$— or —(CH$_2$)$_2$O(CH$_2$)$_2$—;

Y denotes CH$_2$ or (CH$_2$)$_2$;

Z denotes 0 or H$_2$;

Ar denotes unsubstituted or mono- to 5-substituted phenyl [wherein the substituents of the phenyl independently of one another denote halogen (F, Cl, Br, I), OH, (C$_1$–C)alkyl, O—(C$_1$–$_4$)alkyl, CF$_3$, OCF$_3$ or NR$^9$R$^{10}$ (wherein R$^9$ and R$^{10}$ independently of one another denote H, methyl or acetyl)] or Ar is phenyl substituted by —OCH$_2$O— or —O(CH$_2$)$_2$O—;

$R^1$ denotes phenyl(C$_1$–$_4$)alkyl or phenyl(C$_1$–$_4$)alkanoyl, wherein phenyl may be substituted by 1 to 3 substituents, wherein the substituents independently of one another denote halogen (F, Cl, Br, I), (C$_1$–$_4$)alkyl, O—(C$_1$–$_4$)alkyl, CF$_3$, OCF$_3$ or NR$^{19}$R$^{20}$ (wherein R$^{19}$ and R$^{20}$ independently of one another denote H, methyl or acetyl); and $R^2$ denotes H, (C$_1$–$_4$)alkyl or (C$_3$–$_6$)cycloalkyl.

Particularly preferred are those compounds wherein

X denotes N—$R^3$ or CH—$R^4$, wherein $R^3$ denotes

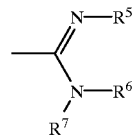

and $R^4$ denotes

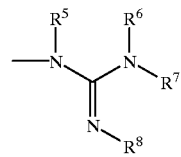

and $R^5$ to $R^8$, Z, Ar, $R^1$ and $R^2$ are as hereinbefore defined, and Y denotes CH$_2$.

Of these compounds, the preferred ones are those wherein Z is oxo, and/or Ar is unsubstituted phenyl, particularly those wherein Ar is phenyl mono- or disubstituted by halogen, preferably Ar is dichlorophenyl; and/or wherein $R^1$ denotes substituted phenylacetyl (preferably 3,4-di-trifluoromethylphenyl-acetyl) or wherein $R^1$ is substituted phenylethyl, wherein the phenyl is substituted by 2 substituents which, independently of one another, denote halogen (F, Cl, Br, I), (C$_1$–$_4$)alkyl or CF$_3$, particularly wherein the substituents of the phenyl are CF$_3$, CH$_3$ or F, (preferably wherein the two substituents of the phenyl are CF$_3$); and/or wherein $R^2$ is (C$_1$–$_4$)alkyl, preferably wherein $R^2$ is methyl.

Compounds of formula I are preferred wherein the group

is

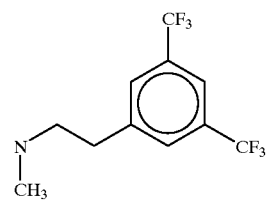

One aspect of the invention relates to compounds of formula I wherein X denotes the group CR$^4$, wherein $R^4$ is

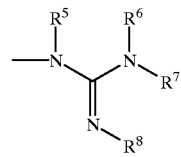

wherein $R^5$, $R^6$, $R^7$ and $R^8$ independently of one another denote H, alkyl with 1 to 4 carbon atoms or cycloalkyl with 3 to 6 carbon atoms; or R⁷ and R⁸ together form the group (CH₂)₂, (CH₂)₃, (CH₂)₄ or (CH₂)₅. Compounds wherein R⁵ and R⁶ denote H and R⁷ and R⁸ together form the group (CH₂)₂ or those wherein R⁵ and R⁶ denote H and R⁷ and R⁸ are cyclohexyl are preferred.

Another important aspect of the invention relates to compounds of formula I wherein X is the group NR³ wherein R¹ is

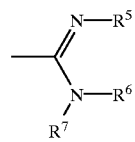

wherein

R⁵ and R⁶ independently of one another denote H, alkyl with 1 to 4 carbon atoms, cycloalkyl with 3 to 6 carbon atoms, phenyl, or phenyl, benzyl or benzoyl substituted by methyl or halogen (F, Cl, Br, I), CN, alkyloxycarbonyl (wherein the alkyl group contains 1 to 4 carbon atoms), benzyloxycarbonyl, alkoxy with 1 to 4 carbon atoms or dialkylamine (wherein the alkyl groups contain 1 to 4 carbon atoms), R⁷ denotes H or alkyl with 1 to 4 carbon atoms; or R⁵ and R⁶ or R⁶ and R⁷ together form the group (CH₂)₂, (CH₂)₃, (CH₂)₄ or (CH₂)₅; or R⁶ and R⁷ together form the group —(CH)₂—O—(CH₂)₂—.

Of these compounds, the preferred ones are those wherein
a) R⁵ and R⁶ independently of one another denote H, alkyl with 1 to 4 carbon atoms, cycloalkyl with 3 to 6 carbon atoms, phenyl, phenyl, benzyl or benzoyl substituted by methyl or halogen (F, Cl, Br, I); R⁷ is H or alkyl with 1 to 4 carbon atoms or R⁵ and R⁶ or R⁶ and R⁷ together form the group (CH₂)₂, (CH₂)₃, (CH₂)₄ or (CH₂)₅; or R₆ and R⁷ together form the group —(CH₂)₂—O—(CH₂)₂—;
b) R⁵ and R⁶ independently of one another denote H, alkyl with 1 to 4 carbon atoms, cyclohexyl, phenyl, methyl-substituted phenyl, benzyl or benzoyl;
R⁷ is H or methyl; or
R⁵ and R⁶ together form the group (CH₂)₂ or R⁶ and R⁷ together form the group (CH₂)₅ or —(CH)₂—O—(CH₂)₂—;
c) R⁵ denotes H, alkyl with 1 to 4 carbon atoms, cyclohexyl, methyl-substituted phenyl, benzyl or benzoyl;
R⁶ denotes H, alkyl with 1 to 3 carbon atoms, cyclohexyl, phenyl, methyl-substituted phenyl or benzyl;
R⁷ is H or methyl; or
R⁵ and R⁶ together form the group —(CH₂)₂— or R⁶ and R⁷ together form the group (CH₂)₂—O —(CH₂)₂—;
d) R⁵ and R⁶ independently of one another denote H, CH₃, CH(CH₃)₂, phenyl or benzyl, R⁷ is H or CH₃, or R⁵ and R⁶ together form the group —CH₂CH₂— or R⁶ and R⁷ together form the group —(CH₂)₂—O—(CH₂)₂—.

Particularly preferred are compounds of general formula I, wherein X denotes the group

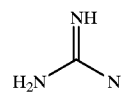

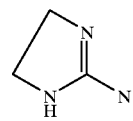

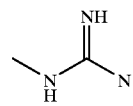

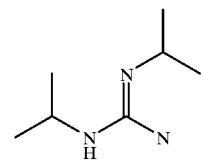

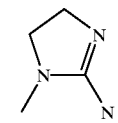

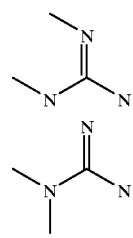

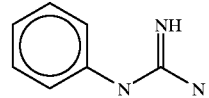

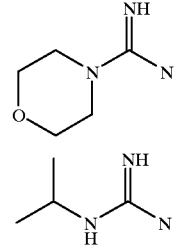

or

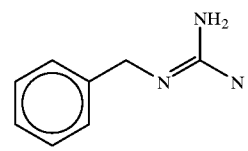

The following compounds are particularly preferred:
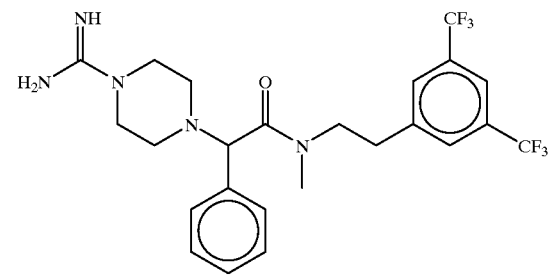
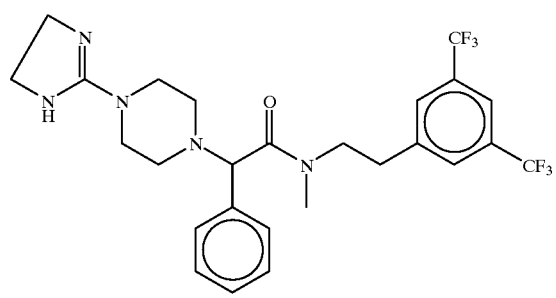
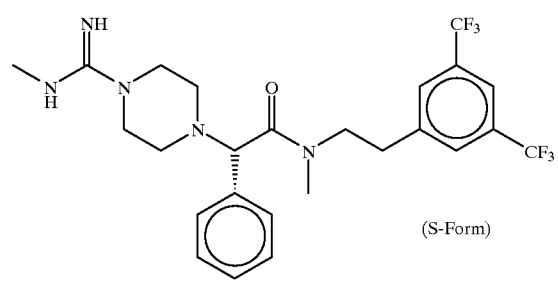
(S-Form)
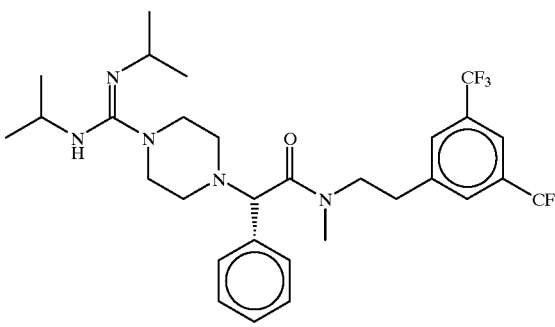
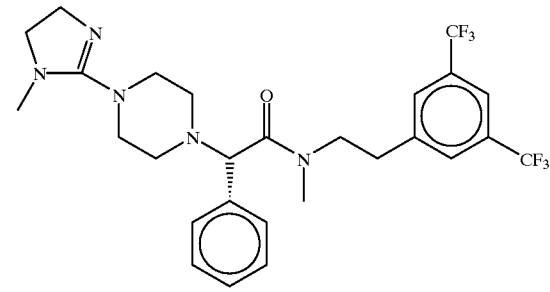
-continued
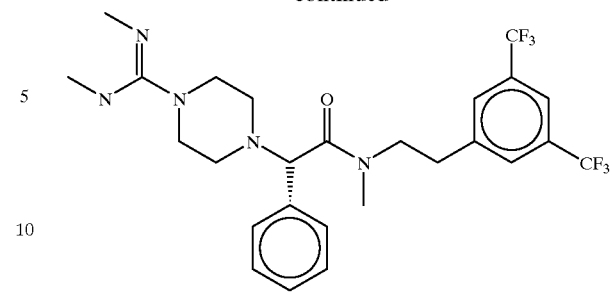
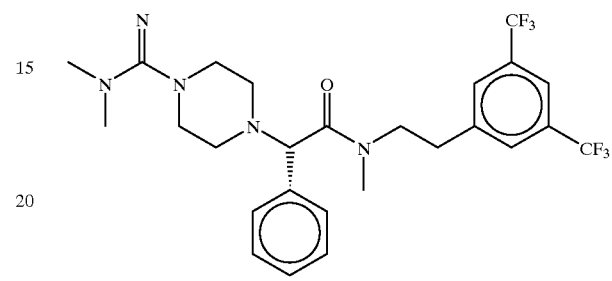
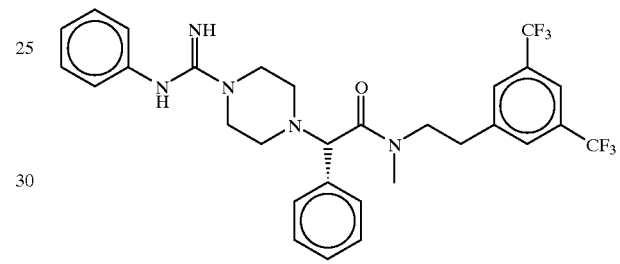
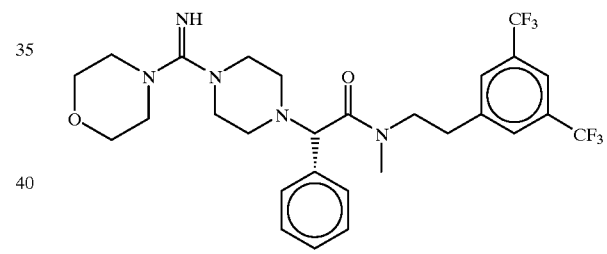
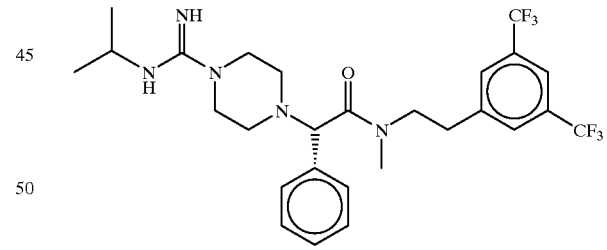
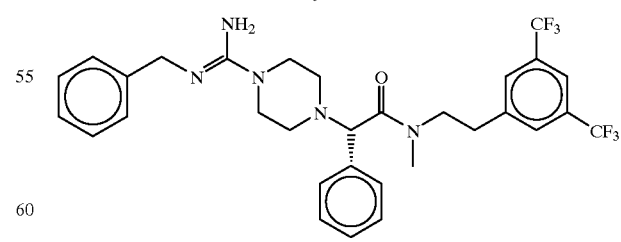
The compounds may be prepared by methods known per se. Advantageous methods are shown and described in the diagrams which follow.

The compounds of general formula

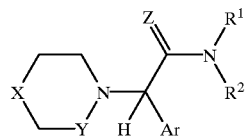

wherein

X denotes N—R³, wherein R³ is

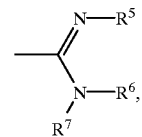

may be prepared by reacting a compound of general formula I wherein R³ denotes hydrogen with the corresponding amino-iminomethanesulphonic acid, the corresponding carbodiimide or thiourea. This process is illustrated by methods A to C for compounds wherein Y is CH₂, Ar is phenyl, Z is oxo, R¹ is difluorophenylethyl and R² is methyl. However, the process can be used analogously for all compounds of formula I wherein X is NR³.

Diagram 1 (method A):

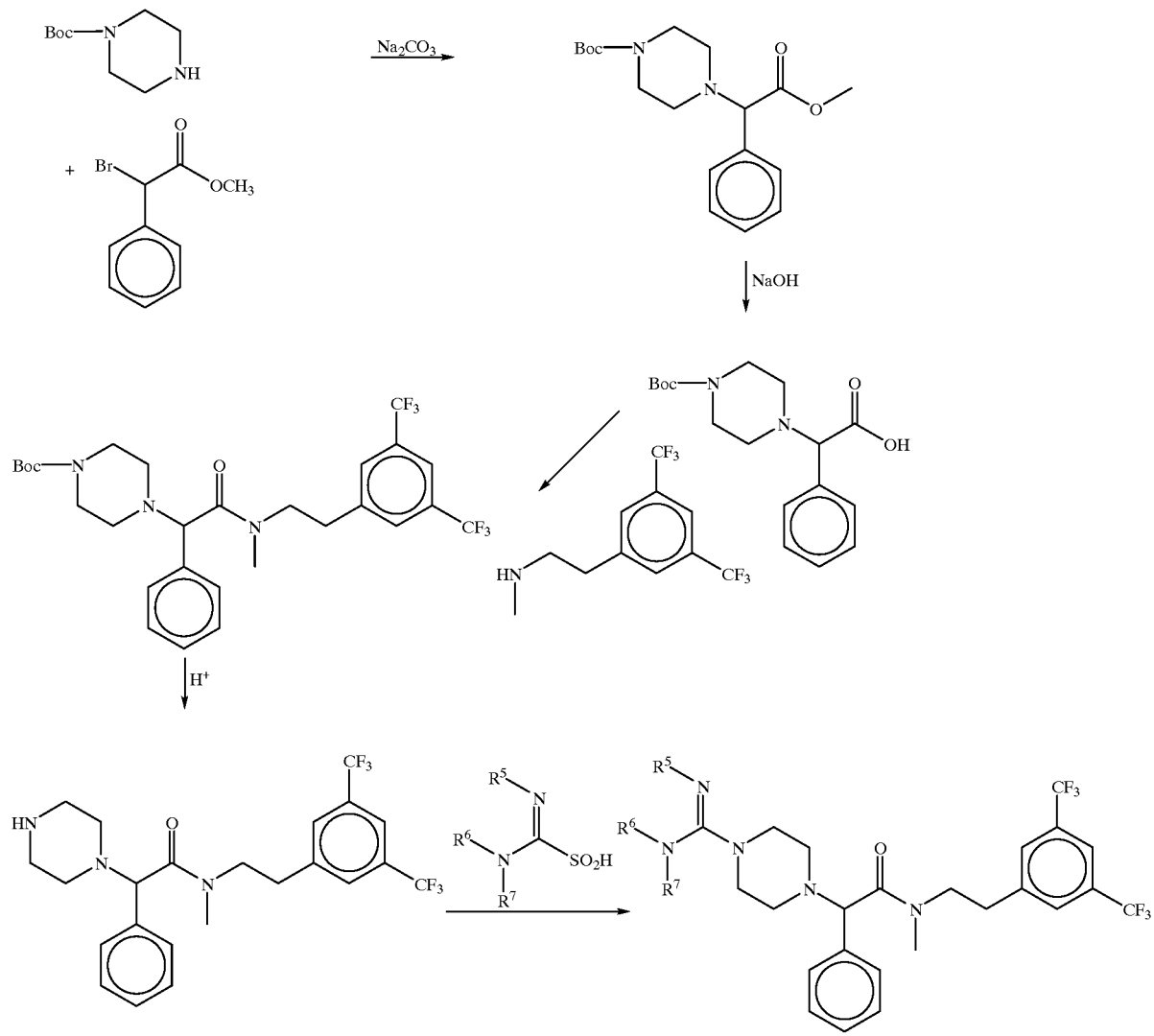

Method A

Piperazine having a protecting group in the 1 position is reacted with 2-halophenyl-acetate to obtain N-protected piperazinyl-phenylacetate. This is saponified under suitable conditions, e.g. with sodium hydroxide solution, to obtain the corresponding carboxylic acid. This is then linked to an amine according to the invention, e.g. N-methyl-3,5-bis-trifluoromethylphenethyl-amine, using a suitable coupling reagent such as TBTU. In the next step the protecting group is cleaved from the piperazine part of the molecule using a suitable cleaving reagent. In the last step of the reaction, the free piperazine-N is reacted with unsubstituted or substituted amino-iminomethanesulphonic acid (which is obtained for example by oxidation of the corresponding thiourea using $H_2O_2$) to obtain the desired guanidine. Compounds of the type in Examples 1–3 may advantageously be prepared by method A, for example.

Diagram 2 (method B):

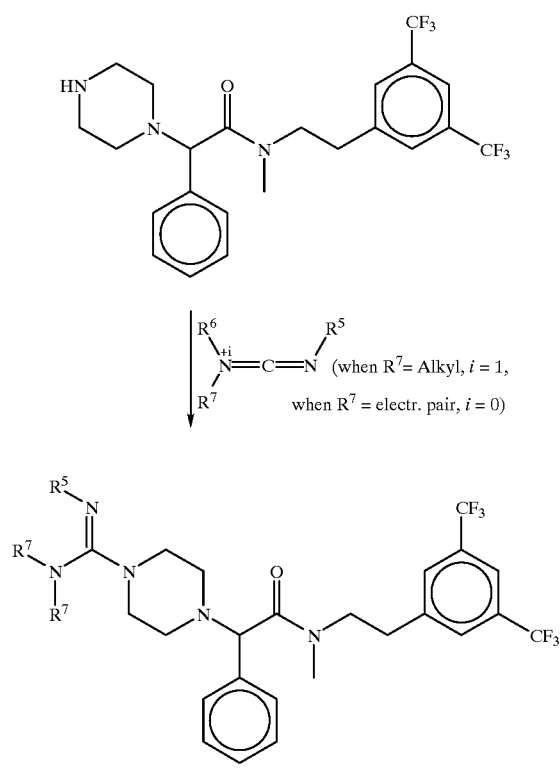

Method B

The same procedure is used as in method A, except that in the last step, the reaction is carried out with carbodiimides instead of the substituted methanesulphonic acid. These may be either N,N'-disubstituted carbodiimides or N,N,N'-trisubstituted carbodiimides, which are then used in the form of a salt, e.g. the iodide.

The compounds of the type in Examples 4 to 7 may advantageously be prepared according to method B, for example.

Diagram 3 (method C):

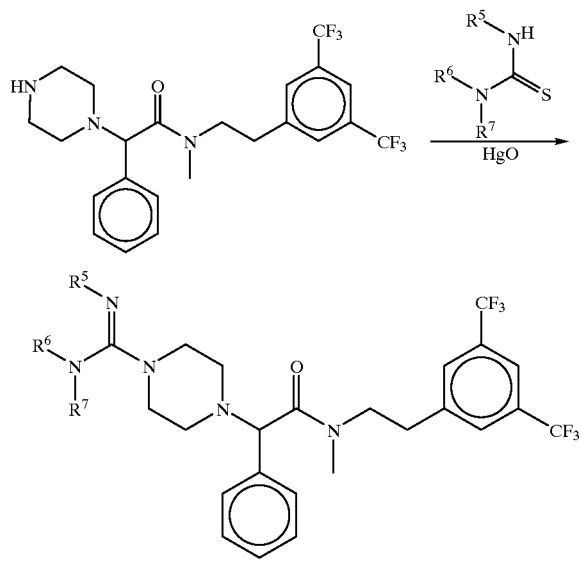

Method C

The same procedure is used as in method A, except that in the last step, instead of the substituted methanesulphonic acid, a substituted thiourea is reacted together with $H_gO$.

Compounds of the type in Example 9 may advantageously be prepared according to method C, for example.

The compound of general formula

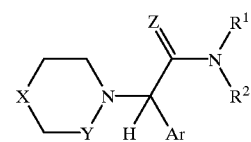

I may also be prepared by reacting the corresponding piperazine derivative or piperidine derivative with the corresponding amide. This process is illutrated by method D and analogous method E for compounds wherein Y denotes $CH_2$, Ar is phenyl, Z is oxo, $R^1$ is difluorophenylethyl and $R^2$ is methyl. The process may be used analogously, however, for all compounds of formula I wherein X is $NR^3$ or $CR^4$. Particularly prefered are compounds wherein $R^3$ denotes

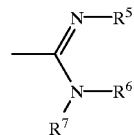

or $R^4$ denotes
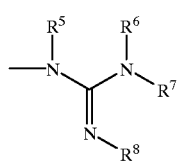
The reaction is carried out in an inert solvent in the presence of a base.
Diagram 4 (method D):
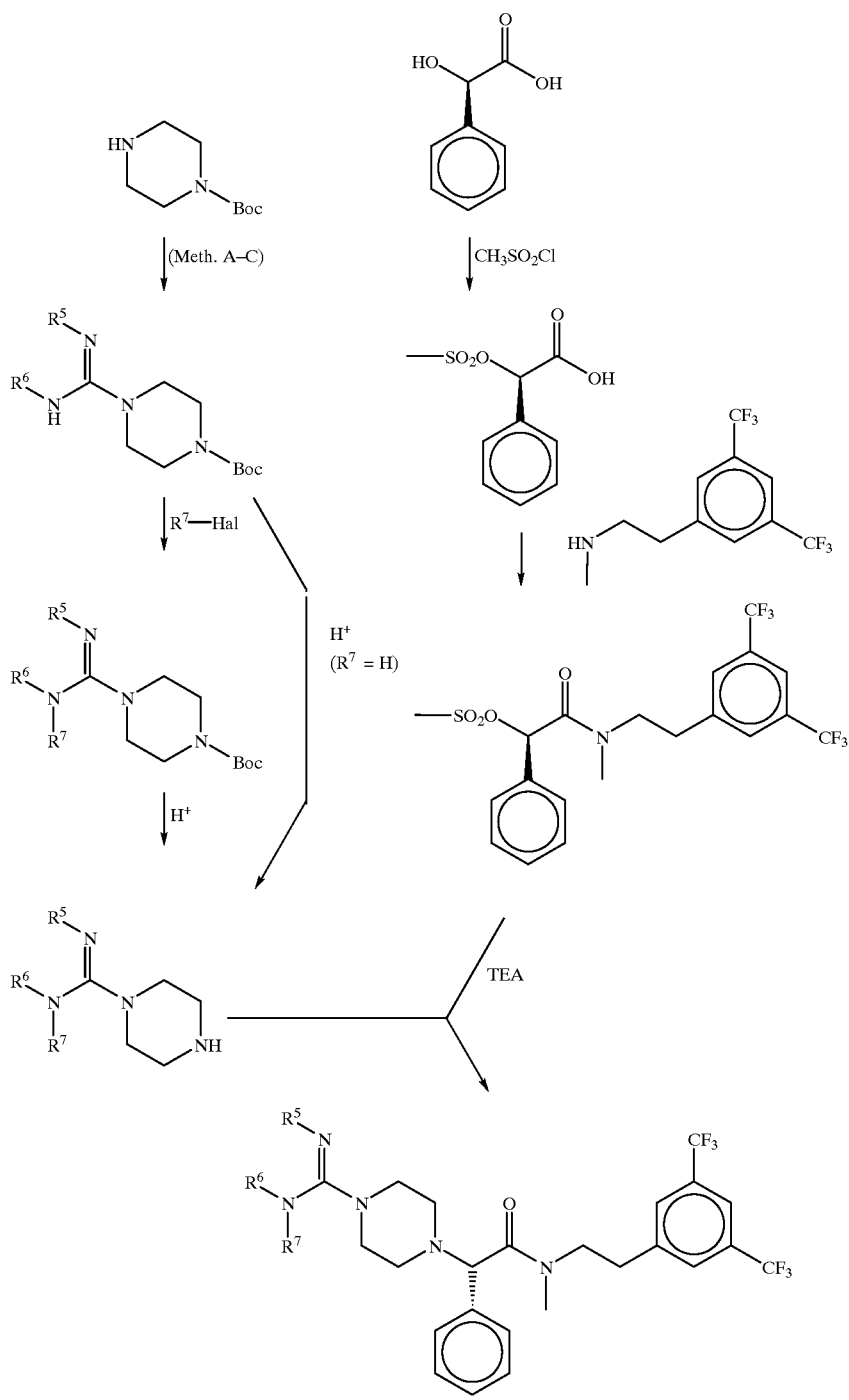

Method D

Analogously to the last step in method A, first of all, piperazine protected in the 1 position is reacted with unsubstituted or substituted amino-iminomethanesulphonic acid. Other substituents may be introduced into the resulting guanidine by alkylation or acylation if required. In the next step the piperazine derivative is obtained with an unsubstituted piperazine-N by cleaving the protecting group with a cleaving reagent.

The reactant for this piperazine derivative is obtained as shown on the right in Diagram 4. (R)-Mandelic acid is reacted with methanesulphonic acid halide to obtain the (R)-2-(methanesulphonyloxy)-acetic acid. This is then reacted with a coupling reagent and the correspondingly substituted phenethylamine to form the corresponding amide, or it is converted into the corresponding acid halide (e.g. with $SOCl_2/SO_2Cl_2$) and then converted, with the suitably substituted phenethylamine, into the corresponding amide. In the last step the amide thus obtained is reacted with the piperazine derivative described above, whereupon a C—N bond is formed, with elimination of methanesulphonate, whilst at the same time the chiral centre is reversed. The reaction is carried out in an inert solvent such as e.g. DMF or acetonitrile in the presence of a base such as TEA or N-methylmorpholine, for example, at temperatures between 20° C. and 120° C. The reaction time is between 0.5 h and 48 h.

Compounds of the type in Example 8 may advantageously be synthesised according to method D.

Scheme 5 (Method E):

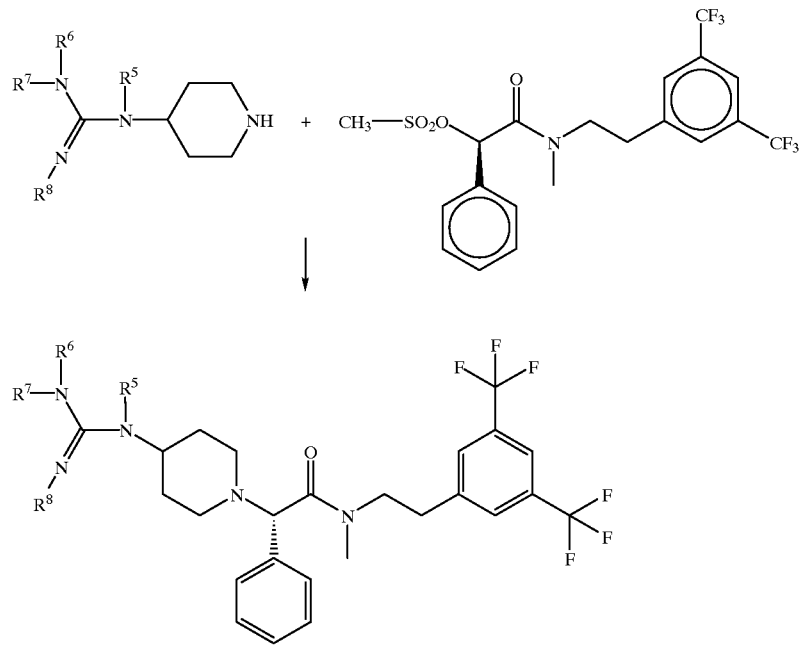

The method is carried out analogously to method D. Compounds of the type in Example 36 may advantageously be synthesised according to Method E.

EXAMPLES

Example 1

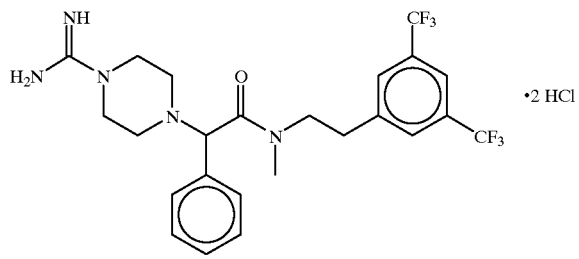

(R,S)-1-Amidino-4-[2-phenylacetic acid-N-methyl-N-(3,5-bis-trifluoromethyl-phenyl-ethyl)-amide]-piperazine, dihydrochloride 1.09 g of (R,S)-1-[2-phenylacetic acid-N-methyl-N-(3,5-bis-trifluoromethyl-phenylethyl)-amide]-piperazine (2 mmol) were mixed with 5 ml of water, 5 ml of methanol, 1.1 g of $K_2CO_3$ (8 mmol) and 0.5 g of aminoiminomethanesulphonic acid (4 mmol) and stirred for 2 days at RT. The reaction mixture was diluted with water and extracted several times with EE and ether. The organic phases were combined, dried with $MgSO_4$ and evaporated to dryness. The solid residue was chromatographed over silica gel and the fractions found to be uniform by DC were combined and evaporated to dryness. The residue was dissolved in methanol, mixed with ethereal HCl, evaporated to dryness, stirred with ether, suction filtered and dried. 80 mg of the compound of Example 1 are obtained (yield 7%).

melting point: 128–138° C.

FAB-MS: $(M+H)^+=516.4$.

Examples 2 and 3 were prepared analogously:

Example 2

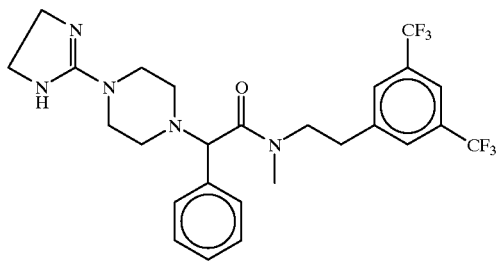

melting point: 163–173° C.
FAB-MS: (M+H)⁺542.2.

Example 3

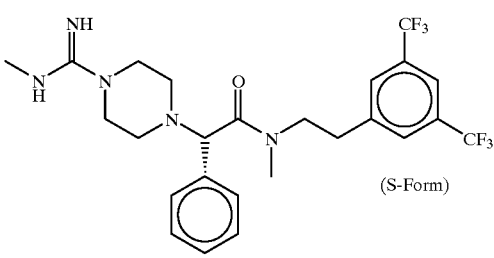

melting point: 69–79° C.
FAB-MS: (M+H)+530.2.

Example 4

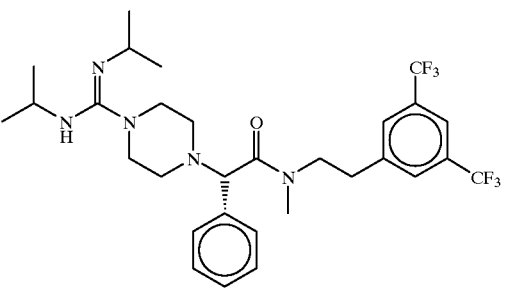

0.82 g of (R,S)-1-[2-phenylacetic acid-N-methyl-N-(3,5-bis-trifluoromethyl-phenylethyl)-amide]-piperazine were mixed with 20 ml of CH$_2$Cl$_2$, 0.5 ml of TEA and 0.215 g of N,N'-diisopropylcarbodiimide and the reaction mixture was stirred for 4 days at RT. It was then evaporated to dryness and the residue was chromatographed over silica gel. The fractions found to be uniform by DC were combined and concentrated by evaporation, the residue was taken up in methanol, mixed with ethereal HCl and again evaporated to dryness. The solid residue was stirred with ether, suction filtered and dried, to obtain 0.35 g of the compound of Example 4 as a racemate (yield 35%)

melting point: 176–1860° C. (decomp.)
FAB-MS: (M+H)⁺=600.6.
Examples 5 to 7 were prepared analogously to Example 4.

Example 5

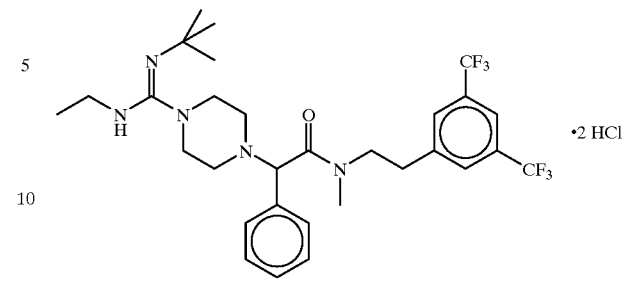

melting point: 174–184° C. (decomp.)

FAB-MS: (M+H)⁺=600.6.

Example 6

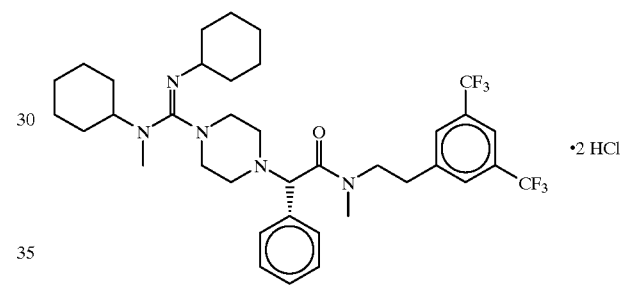

melting point: 145–158° C.

$[\alpha]_D^{20}$=24,80° (DMSO)

Example 7

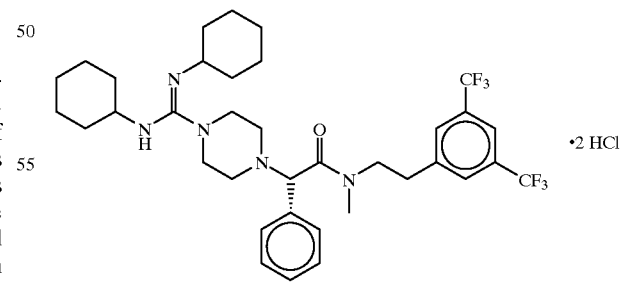

melting point: 182–188° C. (decomp.)

FAB-MS: (M+H)⁺=680.3.

Example 8

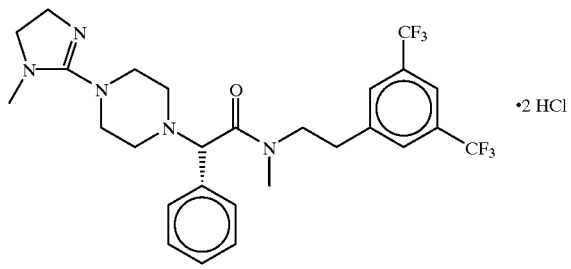

Preparation of 1-(1-methyl-imidazolin-2-yl)-piperazine: 1.86 of Boc-piperazine were combined with 25 ml of water, 25 ml of methanol, 2.77 g of $K_2CO_3$ and 1.5 g of imidazoline-2-sulphonic acid and stirred for 2 days at RT. After dilution with water the mixture was extracted with EE and chromatographed over silica gel. 0.8 g of 1-(imidazolin-2-yl)-4-Boc-piperazine were obtained. This substance was combined with 6.2 ml of DMF and 136 mg of NaH dispersion (60%). After one hour, 0.214 ml of methyl iodide was added dropwise and the reaction mixture was left for three days at RT. It was combined with water, extracted with EE and chromatographed over silica gel. In this way, 0.47 g of 1-(1-methylimidazolin-2-yl)-4-Boc -piperazine was obtained, which was treated with 5 ml of 4N HCl in dioxane at RT. After one hour, the mixture was concentrated by evaporation, stirred with ether and evaporated to dryness in vacuo. 0.38 g of 1-(1-methyl -imidazolin-2-yl)-piperazine dihydrochloride was thus obtained as a solid substance (yield 15%).

0.73 g of (R)-mandelic acid—O-methanesulphonate-N-methyl -N-(3,5-bistrifluoromethylphenylethyl)-amide was combined with 15 ml of DMF, 0.7 ml of TEA and 0.38 g of 1-(1-methyl-imidazolin-2-yl)-piperazine dihydrochloride and stirred for 3 h at 65° C. The reaction mixture was evaporated down, the residue was first treated with $NaHCO_3$ solution and then extracted twice with EE. The organic phases were combined, concentrated by evaporation under reduced pressure and the residue was chromatographed over silica gel. The product thus obtained was dissolved in ether, washed with $NaHCO_3$, and evaporated to dryness with $MgSO_4$.

The residue was dissolved in methanol, mixed with excess ethereal HCl and evaporated to dryness, to obtain 0.18 g of the compound of Example 8 (yield 19%)

melting point: 115–125° C.
FAB-MS: $(M+H)^+=556.9$.

Example 9

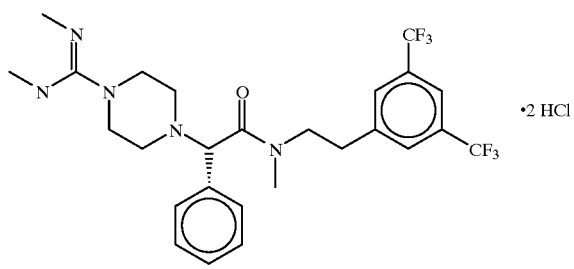

0.31 g of N,N'-dimethylthiourea, 26 ml of $CH_2Cl_2$, 0.63 g of $Na_2SO_4$, 1.25 g of HgO, 0.77 g of (S)-1-[2-phenylacetic acid-N-methyl-N-(3,5-bistrifluoromethyl-phenylethyl)-amide]-piperazine and 0.42 ml of TEA were combined, stirred for 3 days at RT and then refluxed for 4 hours. The reaction mixture was concentrated by evaporation under reduced pressure and the residue was treated with water and EE. The organic phase separated off was filtered and evaporated to dryness. The residue was chromatographed over silica gel. The eluate obtained was evaporated down, dissolved in methanol, mixed with ethereal HCl, evaporated to dryness once more, the residue was washed with ether and dried. 0.15 g of the compound of Example 9 was obtained as a white solid (yield 16%)

melting point: 126–140° C.
FAB-MS: $(M+H)^+=543.8$.

Example 10

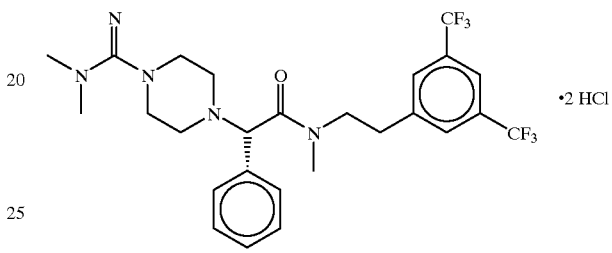

melting point: 131–141° C.
$[\alpha]_D^{20}=20.60$ (DMSO)

The Examples which follow may be prepared using the methods described.

Example 11

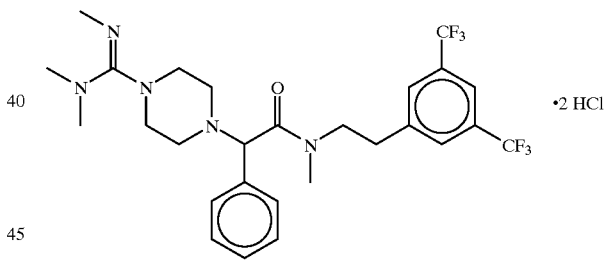

(+)-enantiomer melting point: 171–181° C.
$[\alpha]20/D=28.4°$ (DMSO)

Example 12

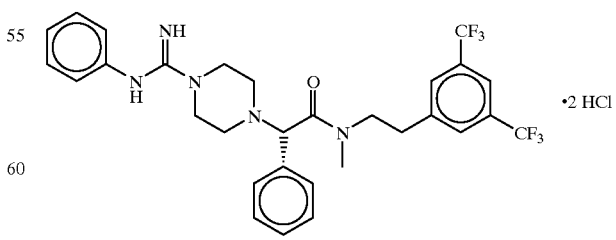

melting point: 240–245° C. (decomp.)
FAB-MS: $(M+H)^+=592.1$.

Example 13
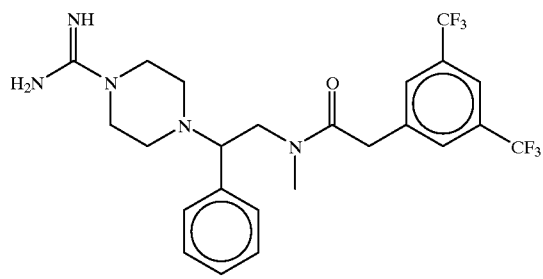
Example 17
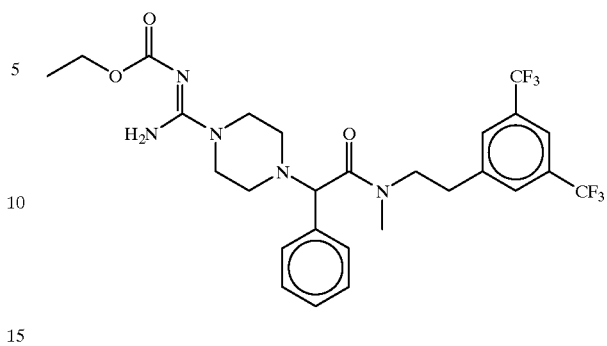
Example 14
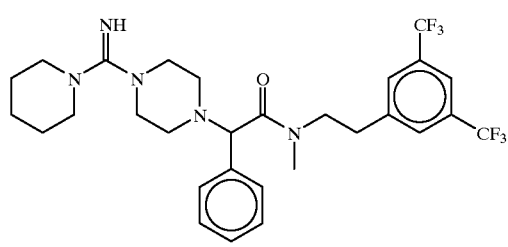
•2 HCl
(+)-enantiomer FAB-MS: (M+H)⁺=584.
Example 18
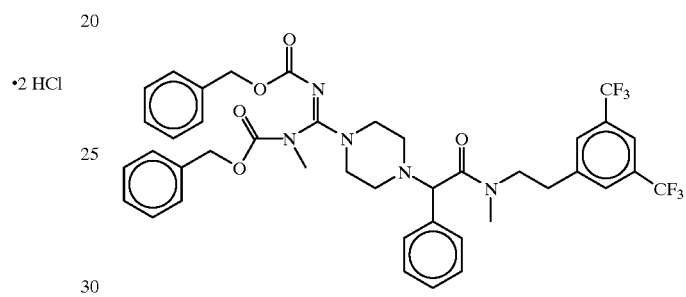
Example 15
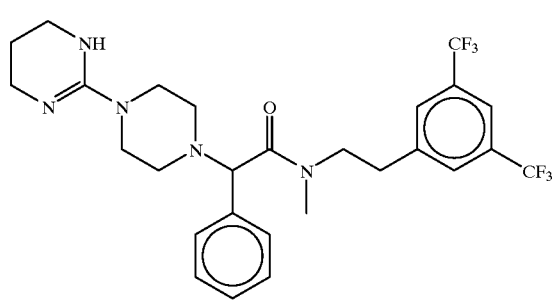
Example 19
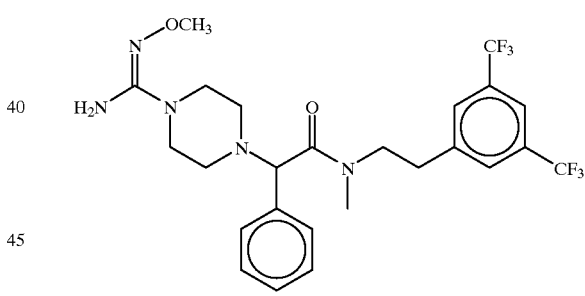
Example 16
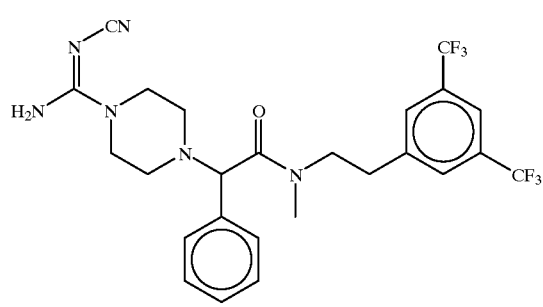
Example 20

Example 21
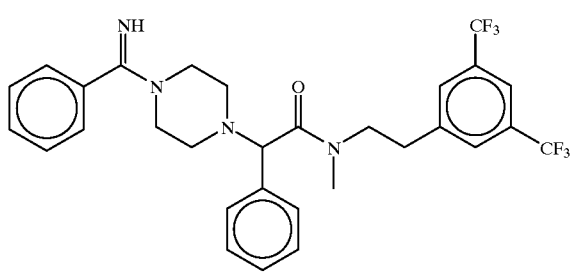
Example 22
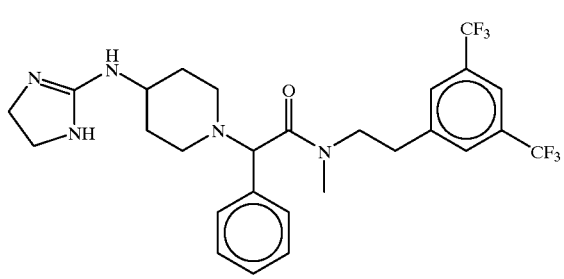
Example 23
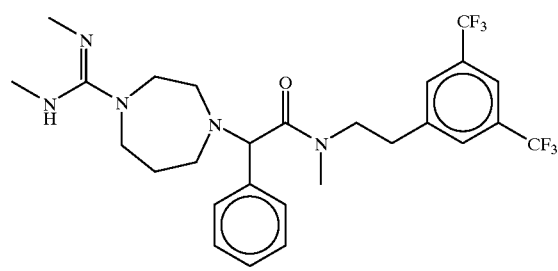
Example 25
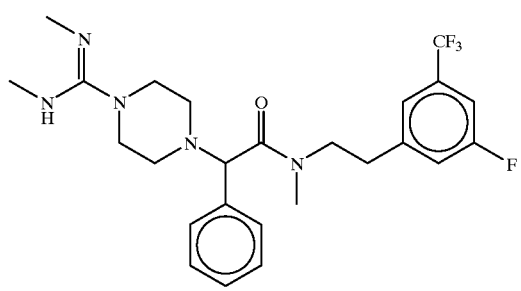
Example 26
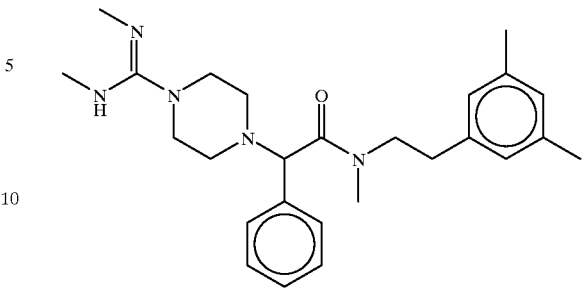
Example 27
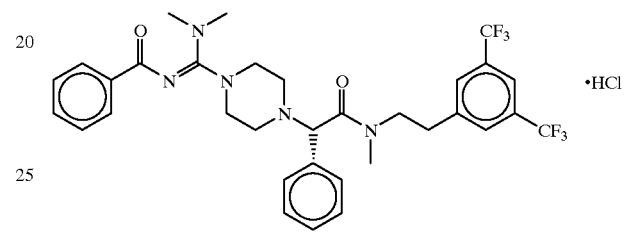
melting point: 124–128° C. FAB-MS: (M+H)$^+$=648.2
Example 28
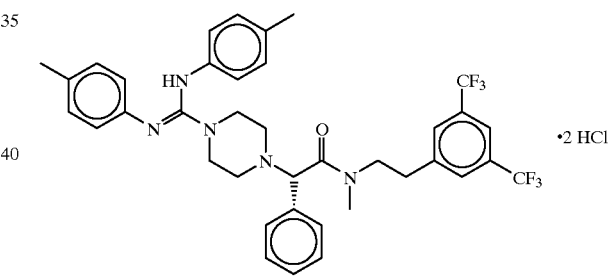
melting point: 193–198° FAB-MS: (M+H)$^+$=696.4
$[\alpha]_D^{20}$=+50.0° (DMSO)
Example 29
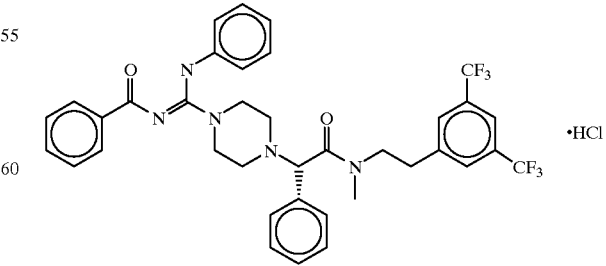
melting point: 146–149° $[\alpha]_D^{20}$+48.8° (DMSO)

Example 30

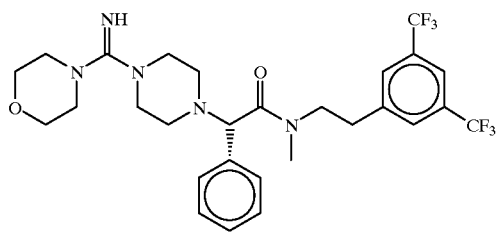

·2 HCl melting point: 90–100° [α]$_D^{20}$=+23.6° (DMSO)

Example 31

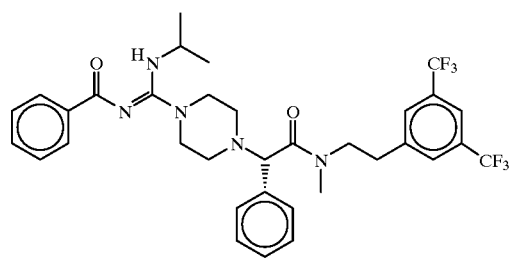

·HCl melting point: 170–1800° FAB-MS: (M+H)$^+$661.9

Example 32

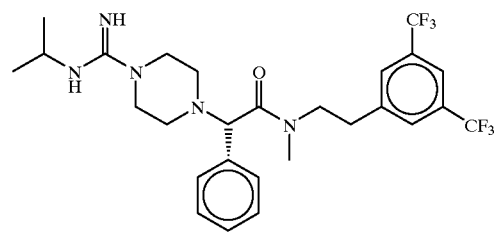

·2 HCl melting point: 84–94° [α]$_D^{20}$=20.4° (DMSO)

Example 33

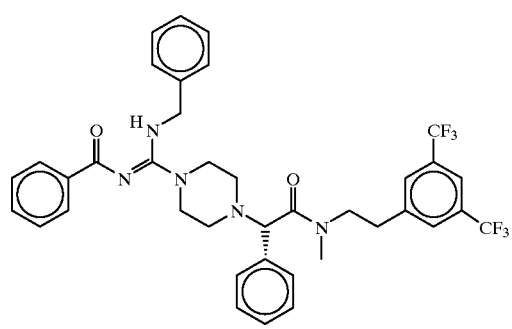

·HCl melting point: 169–179° [α]$_D^{20}$=43.6° (DMSO)

Example 34

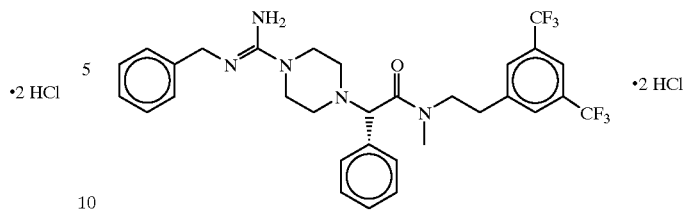

·2 HCl melting point: 131–141° [α]$_D^{20}$+25.2° (DMSO)

Example 35

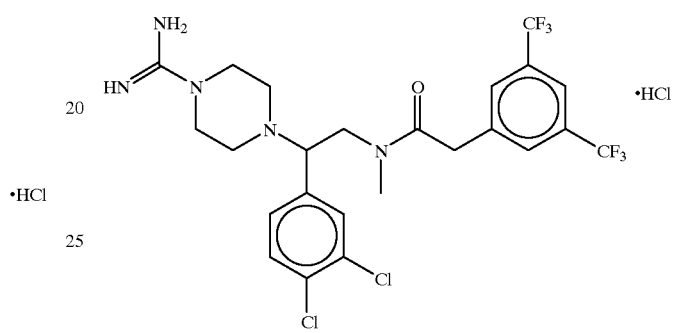

·HCl melting point:146–148° FAB-MS: (M+H)$^+$=584, 586, 588

Example 36

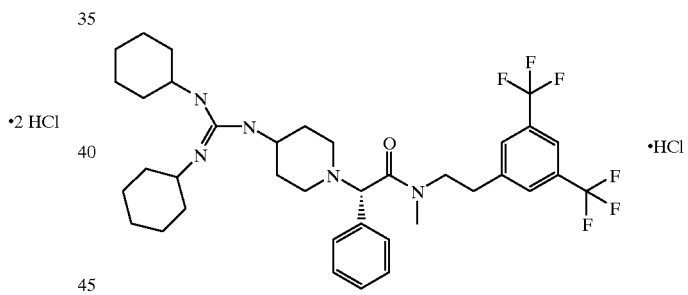

·HCl melting point: 126–134° C.

3.8 g of 4-amino-1-benzylpiperidine (20 mmol) was combined with 4.7 g of dicyclohexylcarbodiimide (23 mmol) in 80 ml of DMF and stirred for 12 hours at 80° C. The solvent was evaporated in vacuo and the residue was flash-chromatographed using ethyl acetate/methanol (1:1) whereby 54. g of 1-benzyl-4(N', N"-dicyclohexyl-guanidino)piperidine was obtained (71%). 5 g of the product (12.6 mmol) was dissolved in 60 ml of methanol and hydrogenated using 0.6 g of Pd(C) at 2 bar hydrogen pressure. Thus obtained was 4 g of 4(N', N"-dicyclohexyl -guanidino)-piperidine (63%). 2.14 g of the product (7 mmol) was combined with 2.9 g of (R)-2-methylsulphonyloxy-N-methyl-N-[2-(3,5-bistrifluoromethyl-phenyl)-ethyl]-phenylacetamide (6 mmol), 60 ml of DMF and 0.96 ml of triethylamine and stirred for 3 hours at 65° C. The residue obtained after concentrating the raw product was chromatographed over silica gel with ethyl acetate/methanol (1:1) as an eluant, whereupon 0.6 g of the desired substance was obtained.

Example 37

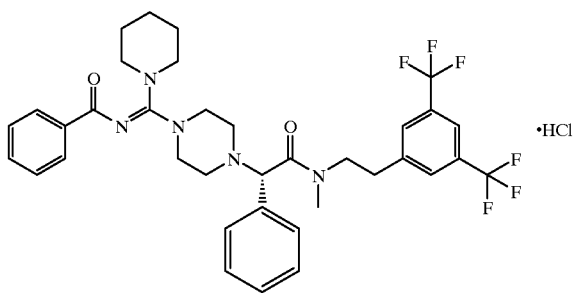

melting point: 114–124° C.

[α]20/D=41.4 (DMSO)

Pharmaceutical Preparations

Injectable Solution

| | |
|---|---|
| 200 mg of active substance * | |
| 1.2 mg of monopotassium dihydrogen phosphate = $KH_2PO_4$ | (buffer) |
| 0.2 mg of disodium hydrogen phosphate = $NaH_2PO_4 \cdot 2H_2O$ | |
| 94 mg of sodium chloride or | (for an isotonic solution) |
| 520 mg of glucose | |
| 4 mg of albumin | (protease protection) |
| q.s. sodium hydroxide solution | |
| q.s. hydrochloric acid | ad pH 6 |
| ad 10 ml water for injections | |

Injectable Solution

| | |
|---|---|
| 200 mg of active substance* | |
| 94 mg of sodium chloride or | |
| 520 mg of glucose | |
| 4 mg of albumin | |
| q.s. sodium hydroxide solution | |
| q.s. hydrochloric acid | ad pH 9 |
| ad 10 ml water for injections | |

Lyophilisate 200 mg of active substance *

520 mg of mannitol (for isotonic solution/bulking agent)

4 mg of albumin solvent 1 for lyophilisate
  10 ml water for injections solvent 2 for lyophilisate
  20 mg Polysorbate®80=Tween®80 (surfactant)
  10 ml water for injections

* active substance: compound according to the invention, e.g. one of Examples 1 to 35

Dosage for person weighing 67 kg: 1 to 500 mg

What is claimed is:

1. Compound of the formula

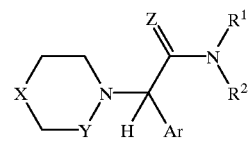

I or the pharmaceutically acceptable salts thereof, wherein
  X denotes CH—$R^4$,
  $R^4$ denotes

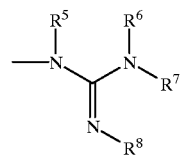

wherein $R^5$ to $R_7$ independently of one another denote H, alkyl, cycloalkyl, alkenyl, aryl, aralkyl, alkanoyl, benzoyl, heteroaryl, dialkylamino, dialkylaminoalkyl, trialkylammoniumalkyl, cyano, alkyloxycarbonyl, aralkyloxycarbonyl, OH, O-alkyl or O-aryl, wherein the alkyl groups contain 1 to 5 carbon atoms, the cycloalkyl groups contain 3 to 6 carbon atoms, the alkenyl groups contain 2 to 5 carbon atoms.

aryl denotes phenyl, or phenyl or naphthyl substituted by methyl, F, Cl, Br or I;
  or $R^5$ and $R^6$ or $R^6$ and $R^7$ together form the group —$(CH_2)_2$—, —$(CH_2)_3$—, —$(CH_2)_4$—, —$(CH_2)_5$— or —$(CH_2)_2$ $O(CH_2)_2$;
  $R^8$=H, alkyl with 1 to 5 carbon atoms or cycloalkyl with 3 to 6 carbon atoms or
  $R^7+R^8$ together form the group —$(CH_2)_2$—, —$(CH_2)_3$—, —$(CH_2)_4$—, —$(CH_2)_5$— or —$(CH_2)_2$ $O(CH_2)_2$—;
  or $R^4$ denotes

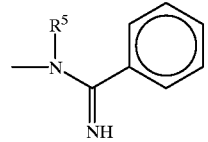

wherein $R^5$ is as hereinbefore defined;
  Y denotes $CH_2$;
  Z denotes O or $H_2$;
  Ar denotes unsubstituted or mono- to 5-substituted phenyl, or unsubstituted or mono- or disubsti-tuted naphthyl wherein the substituents of the phenyl and naphthyl independently of one another denote F, Cl, Br, I, OH, $(C_{1-4})$alkyl, O—$(C_{1-4})$alkyl, $CF_3$, $OCF_3$ or $NR^9R^{10}$ wherein $R^9$ and $R^{10}$ independently of one another denote H, methyl or acetyl or Ar is phenyl substituted by —$OCH_2O$— or —$O(CH_2)_2O$—;
  $R^1$ denotes phenyl$(C_{1-4})$alkyl or phenyl$(C_{1-4})$alkanoyl or naphthyl$(C_{1-4})$alkyl or naphthylacetyl, wherein phenyl may be substituted by 1 to 3 substituents, wherein the substituents independently of one another denote F, Cl, Br, I, $(C_{1-4})$alkyl, O—$(C_{1-4})$alkyl, $CF_3$, $OCF_3$ or $NR^{19}R^{20}$ wherein $R^{19}$ and $R^{20}$ independently of one another denote H, methyl or acetyl; and $R^2$ denotes H, $(C_{1-4})$alkyl, $(C_{3-6})$cycloalkyl, $CH_2COOH$, —$CH_2C(O)NH_2$, OH or phenyl$(C_{1-4})$alkyl.

2. Compound according to one of claim 1, wherein $R^4$ is

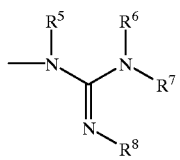

wherein $R^5$, $R^6$, $R^7$ and $R^8$ independently of one another denote H, alkyl with 1 to 4 carbon atoms or cycloalkyl with 3 to 6 carbon atoms; or $R^7$ and $R^8$ together form the group $(CH_2)_2$, $(CH_2)_3$, $(CH_2)_4$ or $(CH_2)_5$.

3. Compound according to claim 2, wherein $R^5$ and $R^6$ denote H and $R^7$ and $R^8$ together form the group $(CH_2)_2$.

4. Compound according to claim 2, wherein $R^5$ and $R^6$ denote H and $R^7$ and $R^8$ denote cyclohexyl.

5. The compound according to claim 1 selected from the group consisting of

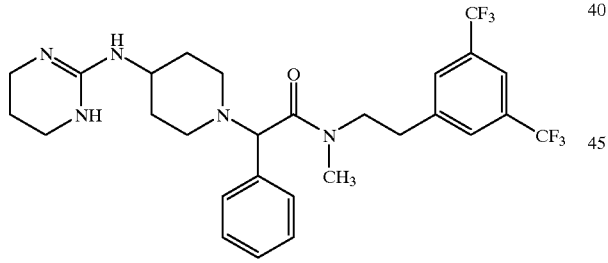

and

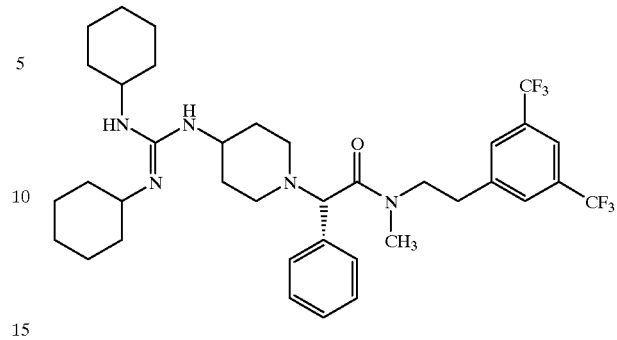

6. A pharmaceutical composition comprising a pharmaceutically effective amount of a compound according to claim 1, a pharmaceutically acceptable carrier and excipient.

7. A process of making a compound of the formula 1 according to claim 1, the process comprising:

a) reacting an amide of the formula

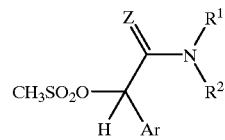

in an inert solvent in the presence of a base with a piperidine of the formula

wherein $R^4$ denotes

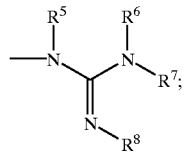

and b) isolating the resulting compound in the free form and in the form of a salt.

* * * * *